United States Patent [19]

Kelton et al.

[11] 4,399,229

[45] Aug. 16, 1983

[54] RAPID RADIOIMMUNOASSAY PRODUCT AND METHOD OF MAKING AND USING SAME

[75] Inventors: Arden A. Kelton, Westminster; Michael L. Bell; Roy A. Chung, both of Newport Beach, all of Calif.

[73] Assignee: Immutron, Inc., Long Beach, Calif.

[21] Appl. No.: 139,770

[22] Filed: Apr. 14, 1980

[51] Int. Cl.$^3$ .................... G01N 33/54; G01N 33/58; G01N 33/60

[52] U.S. Cl. .................................... 436/519; 436/535; 436/542; 436/820; 436/804; 436/828

[58] Field of Search ............................... 424/1, 12, 85; 23/230 B; 435/7

[56] References Cited

U.S. PATENT DOCUMENTS

| | | | |
|---|---|---|---|
| 3,995,018 | 11/1976 | Stöquist | 424/1.5 |
| 4,143,124 | 3/1979 | Masson et al. | 424/1 X |
| 4,166,106 | 8/1979 | Sedlacek et al. | 424/1 X |
| 4,189,464 | 2/1980 | Blumberg et al. | 424/1 |
| 4,223,005 | 9/1980 | Teodorescu et al. | 424/85 X |
| 4,293,538 | 10/1981 | McAleer et al. | 424/1 |

OTHER PUBLICATIONS

Natali et al., *J. Immunol. Methods*, 25, (1979), 255–264.
The Enzyme Center Inc., "IgGSORB-The New ADSORBING AGENT".
Jonsson et al., *Radioimmunoassay and Related Procedures in Medicine*, vol. II, IAEA, Vienna, 1974, pp. 287–298.
Kearney et al., J. Immunology, vol. 114, No. 4, Apr. 1975, pp. 1143–1146.
Kessler, J. Immunology, vol. 115, No. 6, Dec. 1975, pp. 1617–1624.
Kessler, J. Immunology, vol. 117, No. 5, Part I, Nov. 1976, pp. 1482–1490.

*Primary Examiner*—Christine M. Nucker
*Attorney, Agent, or Firm*—Mahoney & Schick

[57] ABSTRACT

A stabilized radioimmunoassay product consisting of an antibody protein-bound to the cell wall of a selected bacterium whereby the antibody is irreversibly bound to the protein and remains specific for the antigen against which it was developed. The radioimmunoassay product is also characterized by the fact that the resultant complete product includes a phase of serum protein treatment to isolate the protein sites or other sites of nonspecific reactivity with the labelled antigen such that the non-specific binding of labelled antigen is significantly reduced. Also within the contemplation of the invention is the method of manufacturing the radioimmunoassay product which includes the initial phase of protein binding of the antibody to the selected bacterium and the subsequent serum treatment to isolate previously unutilized protein sites such that when said sites are subsequently exposed to labelled antigen it will be rejected. Further within the contemplation of the invention is the method of utilizing the aforesaid product to totally eliminate the necessity for the customary incubation stages necessitated by prior art radioimmunoassay techniques.

4 Claims, No Drawings

RAPID RADIOIMMUNOASSAY PRODUCT AND METHOD OF MAKING AND USING SAME

BACKGROUND OF THE INVENTION

The technique of radioimmunoassay had its inception approximately twenty years ago in the study of plasma insulin in human subjects by immunological methods.

Conventional radioimmunoassays are characterized by the necessity for a series of incubation periods whose duration is dependent upon the type of assay being conducted and the type of antigen being subjected to the assay. The necessity for as many as three incubation periods naturally prolongs the time necessitated for the completion of the study. Thus, the final results of the assay are frequently not available until the day following the initiation of the procedure, since some radioimmunoassays take as long as twenty-four hours to complete.

The time lapse occasioned by conventional radioimmunoassays is particularly critical in such cases as cardiac arrest where the subject is placed in intensive care and there may be doubt as to the exact nature of the patient's problem until the results of the radioimmunoassay are made available.

It is not unknown for a patient to succumb before the results of the assay are available which, if available at an earlier time, might have conceivably sharpened the diagnosis and permitted the utilization of techniques which would have saved the life of the patient.

It is well known that many seeming heart arrests are really caused by acute indigestion or vice versa. Frequently, the exact nature of the disorder cannot be determined until the results of the time-consuming radioimmunoassay have been received.

The reason for the lengthy incubation periods lies in the fact that there is an ambivalent hunt and seek of the labelled antigen and unlabelled or serum antigens for sites on the antibody to which the antigens are exposed. Therefore, it takes considerable time for the process to reach comparative stabilization in which the results can be obtained by exposure of the incubated mixture to a gamma count.

For instance, in a standard immunoassay, a standard reference or unknown antigen is admixed in aqueous suspension with a specific antibody and subjected to a first period of incubation. The resultant suspension is then admixed with $125_I$ labelled antigen and a second incubation occurs. The resultant suspension is then admixed with a second antibody or charcoal or ammonium sulfate and is subjected to a third incubation. The completion of the third incubation results in the precipitation of antibody with bound components which are separated by configuration or filtration and the isolated precipitate is then subjected to radioactivity measurement by the use of gamma counters or similar instruments.

A second common procedure involves only the first two incubations of the previously discussed procedure and instead of utilizing a second antibody or equivalent substances, protein A/Staphylococcus aureus is admixed with the product of the second incubation. The steps of the method than include precipitation, separation and measure of radioactivity of isolated precipitate.

In a third form of radioimmunoassay the first incubation occurs with the specific antibody chemically bound to the surface of a particle, test tube or the like. First and second incubations occur as in the previously discussed methods but the resultant suspension of the second incubation is subjected to the binding of a proportion of antigen on the surface-bound antibody. Then the separation and radioactivity measurement steps take place.

As can be readily determined, incubation steps are an inherent part of all of the known methods and the deleterious delay resulting from such necessary incubation steps can result in misdiagnosis and possible consequent loss of life of the patient. Corrollary factors to the necessity for prolonged incubation are the expense of the radioimmunoassay, the amount of wastage of various ingredients including the isotope labelled antigens and the possible error in the assay resulting from the lack of complete binding of antigens on the antibody.

Typical of prior art developments in U.S. Pat. No. 4,107,284 issued Aug. 18, 1978 on a radioimmunoassay procedure using a stabilized complex. The above-referenced patent constituted an attempt to extend the shelf life of a complex of labelled antigen and antibody by the utilization of stabilizers.

Basically, the conventional methodology can be divided into two procedures. First is the mixing of standard, reference or unknown antigens with a specific antibody. Second is the mixing of the first mix with the $125_I$ labelled antigen.

In the first mixture, unlabelled antigens are added to specific antibody. The labelled antigen (tracer) is then added and competes with the unknown, nonlabelled antigen for the binding sites on the antibody. The amount of unknown antigen is thereby inversely proportional to the amount of labelled antigen which is bound to the antibody. Usually, simultaneous procedures are conducted for standard antigens (unlabelled antigens of known concentration) in order to derive a standard curve. The concentration of unknown antigen can then be determined by reference to the standard curve.

When the labelled antigen is added to the antigen-antibody complex, a gradual equilibrium occurs in which the unknown or standard antigen competes and exchanges with the labelled antigen for the binding sites on the antibody. The procedure normally requires that the unknown antigen and the standard antigen behave identically in this ability to compete with and/or displace labelled antigen from specific antibody, but identical behavior between the labelled antigen and the unknown and standard antigen are not required. In conclusion, at least one and usually two lengthy incubations or reagents are required in the first procedure.

Following incubation to form an antigen-antibody complex, the free and bound components are separated. The usual procedure for separation employs a second antibody which has a specific affinity for the first antibody and forms a precipitate. The precipitate is isolated from the free components by centrifugation and decanting the solution containing the free components.

Other methods have been devised to facilitate the separation of antigen-antibody complex from unbound antigen. Many of these involve the binding of antibody to a solid phase, e.g. Sephadex particles, glass beads, plastic beads, test tube surfaces, filter paper, etc.

Another, more recent method for separation of free and bound components employs protein A associated with the cell wall of the bacterium *Staphylococcus aureus*. Protein A has a high affinity for the Fc fragments of IgG molecules of several mammalian species. Thus, these bacteria can be used in place of the second antibody to form a complex with the antigen-antibody complex which can then be isolated by centrifugation and decanting. The reaction rate between the bacterial protein A and IgG is very rapid in comparison to the double antibody technique and represents a substantial advantage.

However, two significant problems are associated with the use of the protein A bearing *Staphylococcus aureus* in this alternative method. First, large amounts of protein A are required since the protein A must remove all of the IgG from the serum sample as well as the IgG of the first antibody. This results in a significant cost penalty. Second, the large amount of bacteria needed for the assay reslts in a very high nonspecific binding of labelled antigen which significantly increases the error of the assay.

OBJECTS AND ADVANTAGES OF THE INVENTION

It is, therefore, an object of our invention to provide a rapid radioimmunoassay product and method of making and using the same which are characterized by the elimination of the prolonged periods of incubation characteristic of other radioimmunoassay products and methods.

An additional object of our invention is the provision of a radioimmunoassay product which includes a stabilized complex including a bacterium having a selected antibody fixed to sites thereof.

A further object of the invention includes a method of providing a stabilized complex of the aforementioned character which includes the steps of creating a selected bacterial suspension and adding to said bacterial suspension an antibody, IgG, which is specific for the antigen to be assayed. The antibody is adsorbed to the sites on the bacteria in the bacterial suspension.

An additional step of the method involves the fixing of the antibody to the sites of the bacterium by a fixitive such as paraformaldehyde. This prevents the loss of the antibody by exchange at the site of specific IgG for the nonspecific IgG that is present in much larger quantities in the blood serum to be tested.

By the practice of the steps of the method outlined hereinabove, a stabilized complex is achieved which is characterized by the irreversible fixation of the selected antibody to the sites of the bacterium to which the antibody has been fixed.

Other objects and advantages of the invention will be apparent to those skilled in the art from the disclosures appearing hereinbelow and it is not intended that the specific delineation of advantages of the stabilized complex, the method of making same or the method of utilizing same be limited to those set forth hereinabove.

DESCRIPTION OF INVENTION

This invention relates to a rapid radioimmunoassay product and method of making and using same, more particularly to an improved assay product and method using antibody and protein irreversibly bound to the protein A bearing bacterium such as *Staphylococcus aureus*.

An admixture containing labelled and unlabelled antigens is briefly mixed with the bacterial complex. Competition between antigens occurs for the antibody sites bound to the protein A. Because of the very high affinity of protein A for the antigen-antibody complex, the antigens are quickly and irreversibly bound to the bacterial complex. Antibody sites which are available to the antigen are quickly saturated.

This results in a proportion of labelled antigen being bound to the complex which can be measured by its radioactivity and which is inversely proportional to the amount of standard or unknown antigen. The amount of unknown antigen can be determined by reference to a curve constructed from measurements of radioactivity corresponding to the various known concentrations of standard antigen.

The invention is an improvement over the standard radioimmunoassay procedure in that the time for binding of the antigens is greatly reduced, there is no requirement for preincubation of labelled antigen and antibody, and the incubation time for addition of a second antibody during assay is eliminated.

The invention is an improvement over previous uses of protein A for radioimmunoassay in that the amount of protein A needed for an assay, the number of steps in any assay, the nonspecific binding of labelled antigen, and cost of an assay are all reduced. Further, the protein A is not used as a second antibody or as a temporary solid phase support for antibody, but as a permanent solid phase support for antibody used in radioimmunoassay.

As a result of the present invention, stat. radioimmunoassay may be conducted on location at most medical facilities. The reagents are packaged in a kit which basically includes premeasured and preprocessed antibody-bacterial complex, mixtures of premeasured standard and labelled antigens, premeasured labelled antigen for combination with test fluid, and mixtures of reference sera and labelled antigen, as necessary for a radioimmunoassay. Using equipment and supplies normally available in laboratories which routinely conduct radioimmunoassay, test fluids may be assayed for most antigens without any significant incubation. In addition, a special kit and machine have been constructed to automatically perform stat. radioimmunoassay. A simple, disposable, inexpensive kit contains all of the reagents, except water, needed to perform one or more assays for unknown antigen(s) in a serum sample or samples. Standard antigens contained within the kit are assayed simultaneously with the serum sample(s) in order to derive a standard curve for determination of the unknown antigen(s). A relatively simple and inexpensive machine performs automatic operations upon the kit and analyzes and displays the data. Technician time and training requirements are greatly reduced.

The preferred form of this invention is a product and method for conducting rapid radioimmunoassay and enables simplified automation of radioimmunoassay.

As is known, normal radioimmunoassay involves a competition of labelled and unlabelled antigen for specific antibody. Since binding between antigen and antibody is partially reversible, prolonged incubation of the reagents is necessary to attain a satisfactory degree of binding. Also, it is usual to mix the unlabelled antigen with antibody solution and incubate prior to the addition of the labelled antigen resulting in additional incubation. Further, a second antibody which is specific for the first antibody is usually added to precipitate the antigen-antibody complex in order to terminate the reaction and to separate the bound and unbound antigens. This step requires additional incubation.

As is further known, the substance known as protein A and associated with the cell wall of the bacterium *Staphylococcus aureus* has been used to replace second antibody in the usual radioimmunoassay procedure, but is required in large amounts and results in a high degree of nonspecific binding of labelled antigen. Also, the bound IgG may be displaced by additional IgG. Protein A associated with *Staphylococcus aureus* has been irreversibly bound to specific antibody for purposes of isolating an antigen, but has not been used to evolve a product or procedure for radioimmunoassay, or to irreversibly bind protein to the bacteria in order to greatly reduce nonspecific binding of labelled antigen.

While the product and method of the present application are described herein as utilized in conjunction with a radioimmunoassay it will be obvious to those skilled in the art that various other types of labelled antigens can be utilized such as enzyme or fluorescent labelled antigens.

By this invention the reaction between antigen and antibody is very rapid and nearly irreversible which greatly reduces or eliminates the incubation time. There is no requirement to preincubate the unlabelled antigen with antibody. There is no need for a second antibody with its associated incubation time. The protein A associated with *Staphylococcus aureus* is not used as a second antibody substitute so that large amounts are not required. The protein A is irreversibly bound to antibody and is used in a process and procedure specifically for radioimmunoassay.

METHOD OF USING STABILIZED COMPLEX

In general, the procedure of this invention involves provision of a combination of reagents which include a premeasured and preprocessed antibody-bacterial complex, mixtures of premeasured labelled and standard antigens, mixtures of premeasured reference solution and labelled antigen, and labelled antigen for combination with test solution. In general, such reagents are provided in a kit for convenient assay.

A measured amount of test solution is first mixed with labelled antigen in a test tube. Next, measured amounts of all required mixtures are individually mixed with measured amounts of the antibody-bacterial complex in test tubes. The reaction is generally complete after mixing so that the bacterial complex may be immediately separated from the unbound components. Separation is easily accomplished by filtration or by centrifugation and decanting the solution from the pellet. The isolated bacterial complexes are then counted for bound radioactivity.

The above procedures are easily automated. An automated procedure of this invention involves trapping the complex of antibody, serum and bacteria in a depth filter, usually of glass microfibre with a retention of approximately 99% of particles of one micron diameter. The labelled and unlabelled antigens are mixed and passed slowly through the filter. The filter is washed and counted for radioactivity. A standard curve is constructed from counts of radioactivity of filters containing labelled antigen that had been mixed with known concentrations of unlabelled antigen and passed through such filters. An unknown amount of labelled antigen mixed with unlabelled antigen is simultaneously passed through such a filter, counted and determined by comparison with the standard curve.

EXAMPLE 1

The invention has been used to measure estriol in serum samples. Clinically, serum estriol, $E_3$, is used to monitor pregnancy. Dysfunction in the fetoplacental unit is usually reflected either as persistently low $E_3$ levels or by a dramatic fall in maternal $E_3$ concentration.

The process of the invention as adapted to measurement of $E_3$ is as follows. First 2 ml of rabbit anti-$E_3$ antibody, 1/550 with no carrier serum is incubated for 15 minutes at room temperature with 0.9 ml of a 10% suspension of formaldehyde-treated and heat-killed staphylocci of strain Cowan I. Next, 4 ml of 0.5% paraformaldehyde in phosphate buffered saline (PBS) is added to the suspension and the next mixture is incubated at 37° C. for 45 minutes. Following incubation, the suspension is centrifuged and resuspended in 4 ml of normal rabbit serum diluted 1:3 with PBS. The bacterial preparation is resuspended by vortexing and incubated 15 minutes at room temperature. Next, 4 ml of 0.5% paraformaldehyde in PBS is added to the suspension and incubated 45 minutes at 37° C. The suspension is diluted to 20 ml by addition of 0.5% of paraformaldehyde in PBS.

The procedure of the invention for usual measurement of $E_3$ is as follows. The kit contains the antibody-bacterial complex as processed and measured. Further, the kit contains standard antigens at concentrations of 0, 5, 10, 20, 40 or 80 ng/ml of $E_3$. The standard antigens are premixed 1:10 with labelled antigen (I-125). The kit also contains reference sera, usually two, premixed with labelled antigen, 1:10. The mixtures are each added 1:10 to an aliquot of antibody-bacterial complex and thoroughly mixed. Duplicates are usually prepared for each mixture. Usually these mixtures are immediately centrifuged and the unbound component is poured from the pellet. The pellets in the tube are counted (gamma emission for $125_I$) complex with the antibody attached to the protein A bearing bacteria. A standard curve is constructed from the standard antigens and the levels of $E_3$ in the test tube sera are determined from the standard curve.

EXAMPLE 2

The process of the invention as adapted to an automated measurement of $E_3$ is as follows. First, 2 ml of rabbit anti-$E_3$ antibody, 1/550 with no carrier serum is incubated for 15 minutes at room temperature with 0.9 ml of a 10% suspension of formaldehyde-treated and heat-killed staphylocci of strain Cowan I. Next, 4 ml of 0.5% paraformaldehyde in phosphate buffered saline (PBS) is added to the suspension and the new mixture is incubated at 37° C. for 45 minutes. Following incubation the suspension is centrifuged and resuspended in 4 ml of normal rabbit serum, diluted 1:3 with PBS. The bacterial preparation is resuspended by vortexing and incubated 15 minutes at room temperature. Next, 4 ml of 0.5% paraformaldehyde in PBS is added to the suspension and incubated 45 minutes at 37° C. The suspension is diluted to 20 ml by addition of 0.5% paraformaldehyde in PBS. Next, 1.0 ml is added to each of 18 filters (13 mm, Whatman glass microfibre filters GF/B) under vacuum.

The procedure of the invention for measurement of $E_3$ is as follows. Standard or test antigen is added 1:10 to labelled, e.g. $125_I$ antigen. The standard antigens contain 0, 5, 10, 20, 40 or 80 ng/ml of $E_3$. Two sera are analyzed in this example. Nine measurements are performed in duplicate. Labelled and unlabelled antigens are mixed and each sample is passed through a prepared filter at a rate of 0.3 ml/min. and washed with PBS at 0.3 ml/min. Total time is approximately 6 minutes. The filters are counted (gamma emission for 125$i$) to determine the proportion of labelled antigen which has complexed with the antibody attached to the protein A bearing bacteria. A standard curve is constructed from the standard antigens and the levels of $E_3$ in the test sera are determined from the standard curve.

Although the two examples, namely Example 1 and Example 2 refer to the incubation of various types of antibodies, such incubation takes place at the manufacturing laboratory in preparing the stabilized bacterium-/antibody/serum complex and no incubation periods are necessary in the field laboratories. Therefore, it can be readily determined by those skilled in the art that the elimination of the presently necessary periods of incubation in the field laboratories will greatly reduce the time and cost of immunoassays conducted in such laboratories as hospital laboratories and the like.

Another important aspect of the invention is its adaptability to automated use as set forth in Example 2 wherein the stabilized bacterium/antibody/serum complex is placed in suspension and then added to a plurality of filters such as the 13 mm, Whatman glass microfibre filters GF/B under vacuum.

In accordance with the automated procedure standard or test antigen is added to labelled antigen and two sera analyzed by pouring the mixture through two of the filters. Labelled and unlabelled antigens are mixed and each sample is passed through a prepared filter, the total time consumed being six minutes.

The filters are then counted (gamma emission for 125$i$) to determine the proportion of labelled antigen which has complexed with the antibody attached to the bacterium. A standard curve is constructed from the standard antigens and the levels of $E_3$ in the test sera are determined from the standard curve.

We claim:

1. In a composite for conducting an immunoassay the combination of: a filter for retaining a bacterium to which an antibody is bound; and said bacterium being entrapped in said filter whereby, when reagents are caused to flow through said filter, said reagents contact said bacterium to facilitate the reaction of said reagents with said antibody.

2. The composite of claim 1 in which said bacterium is deposited out of suspension into said filter.

3. The composite of claim 1 in which said antibody is irreversibly bound to specific receptors of said bacterium.

4. In a method of conducting an immunoassay, the steps of: depositing an antibody bound bacterium in a filter to entrap the same therein; flowing a reagent through said filter to react with said antibody; and detecting the results of the reaction.

* * * * *